United States Patent
Chae et al.

(10) Patent No.: US 8,772,720 B2
(45) Date of Patent: Jul. 8, 2014

(54) SYSTEM AND METHOD FOR MONITORING UNSATURATED ZONE GAS AND NEAR-SURFACE ATMOSPHERE IN REAL TIME BY USING ISOTOPE ANALYZER

(75) Inventors: Gi-Tak Chae, Daejeon (KR); Ki-Sung Sung, Incheon (KR); Jeong-Chan Kim, Daejeon (KR)

(73) Assignee: Korea Institute of Geoscience and Mineral Resources (KR)

( * ) Notice: Subject to any disclaimer, the term of this patent is extended or adjusted under 35 U.S.C. 154(b) by 26 days.

(21) Appl. No.: 13/619,900

(22) Filed: Sep. 14, 2012

(65) Prior Publication Data

US 2013/0335728 A1     Dec. 19, 2013

(30) Foreign Application Priority Data

Jun. 14, 2012  (KR) .................. 10-2012-0063846

(51) Int. Cl.
  *G01N 21/35*   (2014.01)
(52) U.S. Cl.
  CPC ....................................... *G01N 21/35* (2013.01)
  USPC .................. 250/338.1; 250/343; 356/437
(58) Field of Classification Search
  CPC ........................................................ G01N 21/35
  USPC .................. 250/338.1, 343; 356/51, 437
  See application file for complete search history.

(56) References Cited

U.S. PATENT DOCUMENTS

| | | | |
|---|---|---|---|
| 5,552,775 A | * | 9/1996 | Harley ........................ 340/628 |
| 6,486,474 B1 | * | 11/2002 | Owen et al. ............... 250/339.02 |
| 7,326,931 B2 | * | 2/2008 | Frodl et al. ..................... 250/343 |
| 7,704,746 B1 | | 4/2010 | White et al. |
| 2011/0068940 A1 | | 3/2011 | Kim et al. |

FOREIGN PATENT DOCUMENTS

| | | | | |
|---|---|---|---|---|
| JP | 07333129 A | * | 12/1995 | ............... G01N 7/10 |
| JP | 8-210976 | | 8/1996 | |
| JP | 2006-133200 | | 5/2006 | |
| JP | 2006-275940 A | | 10/2006 | |
| JP | 2008-203124 | | 9/2008 | |
| JP | 2010-243178 A | | 10/2010 | |
| JP | 2011-064671 A | | 3/2011 | |
| KR | 10-2011-0031665 | | 3/2011 | |

* cited by examiner

*Primary Examiner* — David Porta
*Assistant Examiner* — Faye Boosalis
(74) *Attorney, Agent, or Firm* — Christie, Parker & Hale, LLP

(57) ABSTRACT

Disclosed are a system and a method for monitoring unsaturated zone gas and near-surface atmosphere in real time by using an isotope analyzer. The system includes a near-surface atmosphere analyzer including a fixing member, a plurality of near-surface gas inlets, a plurality of gas transfer members communicating with the near-surface gas inlets, an analyzing member including an isotope analyzer, which analyzes an isotope of gas transferred through the gas transfer members, a channel connected to the gas transfer members and the analyzing member to select one gas transfer member and to supply gas transferred through the selected gas transfer member to the analyzing member, and a connection member connecting the channel to the analyzing member, a communication device transmitting components of the isotope output from the isotope analyzer, and a monitoring server outputting the components of the isotope transmitted from the communication device.

16 Claims, 4 Drawing Sheets

SYSTEM AND METHOD FOR MONITORING UNSATURATED ZONE GAS AND NEAR-SURFACE ATMOSPHERE IN REAL TIME BY USING ISOTOPE ANALYZER

CROSS-REFERENCE TO RELATED APPLICATION

This application claims the benefit under 35 U.S.C. §119 of Korean patent application no. 10-2012-0063846 filed on Jun. 14, 2012 in the Korean intellectual property office, the entirety of which disclosure is incorporated herein by reference.

BACKGROUND OF THE INVENTION

1. Field of the Invention

The present invention relates to a technology of monitoring unsaturated zone gas and near-surface atmosphere. In more particular, the present invention relates to a system and a method for monitoring unsaturated zone gas and near-surface atmosphere in real time by using an isotope analyzer.

2. Description of the Related Art

In these days, global warming resulting from greenhouse gas has become main issues all over the world. However, due to a current industrial structure based on fossil fuel, a great amount of carbon dioxide ($CO_2$) serving as a main factor of the greenhouse gas causing the global warming is emitted. Accordingly, in order to prevent the global warming, $CO_2$ discharged from manufacturers must be disposed of.

Recently, a carbon capture & storage (CCS) technology, which serves as a main technology to reduce greenhouse gas, has attracted the attention of all countries of the world as a realistic alternative that may reduce the greenhouse gas while maintaining the current economy based on fossil fuel. A geologic storage technology, which is a storage field of the CCS scheme, is a technology in which $CO_2$ is semipermanently stored at the depth of 800 m or more under the ground by capturing the $CO_2$ discharged from the manufacturers.

In order to realize the geologic storage technology, it is important to select a proper land and minimize the leakage of the $CO_2$. In addition, after the $CO_2$ has been injected, the monitoring of the $CO_2$ leakage to the ground surface resulting from various causes is important. If $CO_2$ leaks onto the ground surface, the accident related to human lives may occur, a natural environment may be harmed, and the stability of ground equipment may not be ensured.

Recently, applicable technologies of monitoring CO2 include geophysical monitoring technologies such as elastic wave prospecting, electrical prospecting, gravity prospecting, and the measuring of the temperature and pressure in an injection stratum, a geochemical monitoring technology such as the measuring of the concentration of $CO_2$ on the ground surface or the concentration of $CO_2$ in the underground water, and a technology of monitoring the inner part of a borehole. However, a part of the technologies may not be individually applied due to low reliability. In addition, if all possible monitoring technologies are applied, cost may be excessively required.

Korean Registered Patent No. 10-0999030 (issued on Dec. 1, 2010) discloses "Method for detecting leakage of gas from underground gas storage by pressure monitoring and Underground gas storage system".

SUMMARY OF THE INVENTION

An object of the present invention is to provide a system and a method for monitoring unsaturated zone gas and near-surface atmosphere in real time by using an isotope analyzer, in which the unsaturated zone gas and the near-surface atmosphere can be monitored with reliability in real time by using the isotope analyzer.

In order to accomplish the object of the present invention, according to one aspect of the present invention, there is provided a system for monitoring an unsaturated zone gas and a near-surface atmosphere. The system includes a near-surface atmosphere analyzer including a fixing member erected on a ground surface, a plurality of near-surface gas inlets fixed to the fixing member according to heights of the near-surface gas inlets, a plurality of gas transfer members communicating with the near-surface gas inlets, an analyzing member including an isotope analyzer, which analyzes an isotope of gas transferred through the gas transfer members, a channel connected to the gas transfer members and the analyzing member to select one gas transfer member and to supply gas transferred through the selected gas transfer member to the analyzing member, and a connection member connecting the channel to the analyzing member, a communication device transmitting components of the isotope output from the isotope analyzer, and a monitoring server outputting the components of the isotope transmitted from the communication device.

According to another aspect of the present invention, there is provided a method of monitoring an unsaturated zone gas and a near-surface atmosphere at a land under which $CO_2$ is stored. The method includes measuring concentration of $CO_2$ at an unsaturated zone in a land to be used to store $CO_2$ under a ground according to time slots in a $CO_2$ concentration detector, transmitting the concentration of $CO_2$ to a monitoring server through a communication device, analyzing information of the concentration of $CO_2$ at the unsaturated zone in the monitoring server, and storing a maximum of the concentration of $CO_2$, which is obtained from a nature, as a reference concentration of $CO_2$ at the unsaturated zone, before CO2 is stored under the ground, analyzing isotopes of gas contained in a near-surface atmosphere in an isotope analyzer of a near-surface atmosphere analyzer, measuring the concentration of $CO_2$ at the unsaturated zone in the $CO_2$ concentration detector, and transmitting the concentration of $CO_2$ to the monitoring server through the communication device, after the storage of the $CO_2$ under the ground is started, and comparing the measured concentration of the CO2 with the reference concentration of $CO_2$ in the monitoring server and outputting an normal signal or an abnormal signal.

As described above, according to a system and a method for monitoring unsaturated zone gas and near-surface atmosphere of the present invention, the concentration of $CO_2$ at the unsaturated zone gas and the near-surface atmosphere can be monitored in real time and the isotopes of the unsaturated zone gas and the near-surface atmosphere can be monitored by using an isotope analyzer, thereby economically observing the behavior of gas including $CO_2$ with reliability in real time.

If the system and the method for monitoring unsaturated zone gas and near-surface atmosphere of the present invention are applied to the monitoring of a land under which $CO_2$ is stored, the action according to the leakage of $CO_2$ stored under the ground can be rapidly performed, and the stability of ground equipment can be ensured.

DETAILED DESCRIPTION OF THE INVENTION

The advantages, the features, and schemes of achieving the advantages and features will be apparently comprehended by those skilled in the art based on the embodiments, which are detailed later in detail, together with accompanying drawings. The present invention is not limited to the following embodiments but includes various applications and modifications. The embodiments will make the disclosure of the present invention complete, and allow those skilled in the art to completely comprehend the scope of the present invention.

Hereinafter, a system and a method of monitoring unsaturated zone gas and near-surface atmosphere in real time by using an isotope analyzer according to the embodiment of the present invention will be described.

Figure 1:
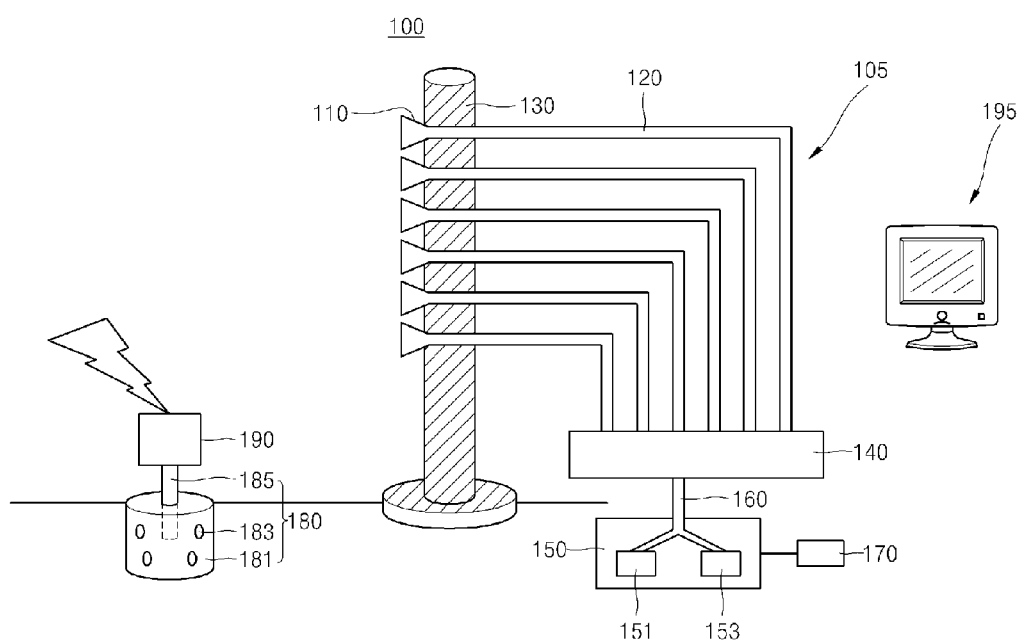
FIG. 1 is a schematic view showing a system for monitoring unsaturated zone gas, and the concentration of carbon dioxide and isotopes at the near-surface atmosphere according to the present invention.
Figure 2:
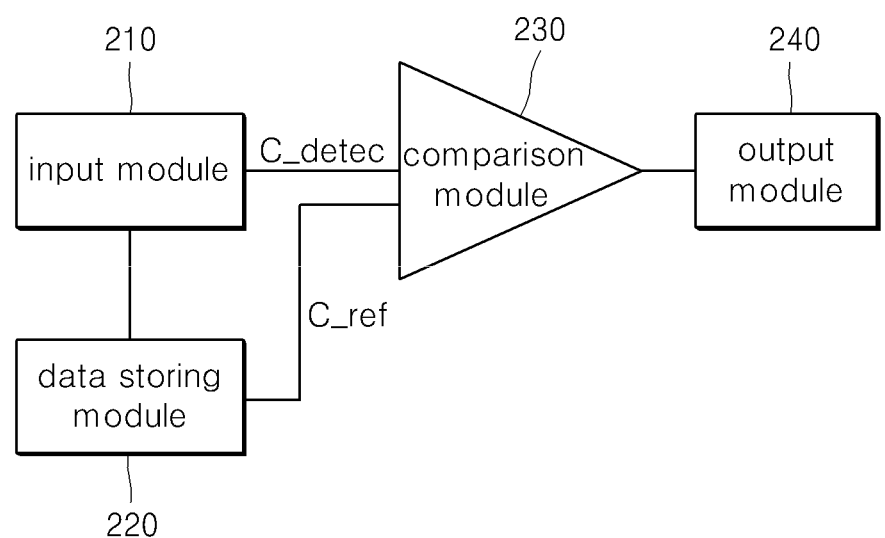
FIG. 2 is a block diagram schematically showing a monitoring server of FIG. 1.

FIG. 1 is a schematic view showing a system 100 for monitoring unsaturated zone gas, and the concentration of carbon dioxide ($CO_2$) and isotopes at the near-surface atmosphere according to the present invention, and FIG. 2 is a block diagram schematically showing a monitoring server of FIG. 1.

Referring to FIG. 1, the system 100 for monitoring unsaturated zone gas, and the concentration of $CO_2$ and isotopes at the near-surface atmosphere mainly includes a near-surface atmosphere analyzer 105, a near-surface atmosphere communication device 170, an unsaturated zone $CO_2$ concentration detector 180, an unsaturated zone communication device 190, and a monitoring server 195.

The near-surface atmosphere analyzer 105 analyzes isotopes or the concentration of $CO_2$ at the near-surface atmosphere, and includes a near-surface atmosphere gas inlet 110, a gas transfer member 120, a fixing member 130, a channel 140, an analyzing member 150, and a connection member 160.

The near-surface atmosphere gas inlet 110 introduces gas including carbon dioxide ($CO_2$), methanol ($CH_4$), vapor ($H_2O$), sulfiding gas ($SO_X$), and hydrogen sulfide ($H_2S$) contained in near-surface atmosphere into the gas transfer member 120. The near-surface atmosphere gas inlet 110 may have the shape of a funnel, and may be fixed to the fixing member 130 having the shape of a column erected on the ground surface. In this case, the near-surface atmosphere refers to the ground surface and the atmosphere. The region of the near-surface atmosphere refers to a region within the range of about 2 m from the ground surface. If necessary, the near-surface atmosphere gas inlet 110 and the fixing member 130 may be installed at the near-surface atmosphere existing at the height of more than 2 m.

The gas transfer member 120 has the shape of a tube communicating with the near-surface atmosphere gas inlet 110 and transfers the gas introduced through the near-surface atmosphere gas inlet 110 to the channel 140. In this case, a portion of the gas transfer member 120 adjacent to the near-surface atmosphere gas inlet 110 may be fixed by the fixing member 130.

The gas transfer member 120 may include a tube having the whole length of 10 m or less, preferably, the whole length of about 1 m to 2 m in order to prevent gas, which has been introduced during the transfer process, from being denaturalized.

A plurality of near-surface gas inlets 110 and a plurality of gas transfer members 120 are formed at different heights from the ground surface.

The channel 140 is connected to the gas transfer members 120, selects one of the gas transfer members 120, and supplies gas, which is transferred through the selected gas transfer member 120, to the analyzing member 150 through the connection member 160. The channel 140 may supply gas transferred through one gas transfer member 120, which is selected in real time according to preset sequences, to the analyzing member 150.

The analyzing member 150 is connected to the channel 140 through the connection member 160 to analyze the gas supplied from the channel 140 through the connection member 160.

In detail, the analyzing member 150 may include a near-surface atmosphere $CO_2$ concentration measuring sensor 151 and an isotope analyzer 153.

The near-surface atmosphere $CO_2$ concentration measuring sensor 151 preferably includes a non dispersive infra-red (NDIR) sensor. The NDIR sensor is a sensor to measure the content of CO2 contained in a gas sample acquired from the near-surface atmosphere, can be easily handled, and can improve the accuracy of the measurement.

The isotope analyzer 153 analyzes isotopes in a gas sample including at least one of $CO_2$, $CH_4$, $H_2O$, $SO_X$, and $H_2S$ contained in the near-surface atmosphere. The isotope analyzer 153 may employ one of a wavelength-scanned cavity ring down spectroscopy (WS-CRDS) scheme and an integrated cavity output spectroscopy (ICOS) scheme.

When analyzing the isotopes of the gas contained in the near-surface atmosphere by using the isotope analyzer 153, the cost is more reduced, and the behavior of the gas can be observed in more detail by analyzing the isotopes of the gas such as $CO_2$, $CH_4$, $H_2O$, $SO_X$, and $H_2S$ contained in the near-surface atmosphere in real time.

In particular, when both of the isotope analyzer 153 and the near-surface atmosphere $CO_2$ concentration measuring sensor 151 are employed, the behavior of the gas, especially, $CO_2$ contained in the near-surface atmosphere can be observed with reliability in real time.

The near-surface atmosphere communication device 170 is connected to the analyzing member 150 to transmit the information of the $CO_2$ concentration of the near-surface atmosphere, which is output from the near-surface atmosphere $CO_2$ concentration measuring sensor 151, and the information of the components of the isotopes, which is output from the isotope analyzer 153, to the monitoring server 195 through wired communication or wireless communication.

The unsaturated zone $CO_2$ concentration detector 180 includes a chamber 181, an unsaturated zone gas inlet 183, and an unsaturated zone $CO_2$ concentration measuring sensor 185.

The chamber 181 includes stainless steel, and is buried in the unsaturated zone under the ground surface. The chamber 181 has the shape of a tub such as a cylindrical tub or a rectangular tub. The chamber 181 is provided in the floor thereof with drain holes (not shown) to naturally drain underground water or soil water by gravity when the underground water or the soil water is introduced into the chamber 181. In this case, the unsaturated zone refers to an upper layer of the surface of the underground water, and, generally, refers to a layer in which rocks and soils are distributed in the uncemented state and gas (oxygen ($O_2$), nitrogen ($N_2$), and carbon dioxide ($CO_2$)) and moisture exist in the soil together. The unsaturated zone may be located in the range of about 50 cm to about 100 cm downward from the ground surface.

At least one unsaturated zone gas inlet 183 is formed at a lateral side of the chamber 181 in the shape of a mesh, so that the gas around the unsaturated zone is introduced into the chamber 181.

The unsaturated zone $CO_2$ concentration measuring sensor 185 is formed through an upper portion of the chamber 181 to measure the concentration of $CO_2$ contained in the gas of the chamber 181. In this case, the unsaturated zone $CO_2$ concentration measuring sensor 185 preferably includes an NDIR sensor which can be easily handled and can enhance the accuracy of the measurement.

However, when the NDIR sensor is installed in the soil, the content of gas in the air gap of the soil is heterogeneous, so that the $CO_2$ concentration may be imperfectly measured. Therefore, according to the present invention, the chamber 181 to collect the predetermined quantity of gas is installed in the soil and the $CO_2$ concentration is measured with respect to gas, which is captured in the chamber 181 and averagely distributed, by using the NDIR sensor.

Meanwhile, the NDIR sensor for measuring the unsaturated zone $CO_2$ concentration may be connected to the analyzing member 150 for measuring the gas concentration of the near-surface atmosphere to measure isotopes existing in the unsaturated zone or isotopes of the gas existing in the unsaturated zone by using the isotope analyzer 153. In this case, the behavior of the gas such as $CO_2$, $CH_4$, $H_2O$, $SO_x$, and $H_2S$ contained in the near-surface atmosphere can be observed in detail in real time.

Once $CO_2$ leaks onto the ground surface, the $CO_2$ is mixed with the atmosphere on the ground surface so that the $CO_2$ is rapidly moved. Accordingly, it is difficult to determine the operation of facilities on the ground by rapidly detecting the concentration of the $CO_2$ and determining the leakage of the $CO_2$. The concentration of the $CO_2$ must be monitored in the unsaturated zone before the $CO_2$ leaks onto the ground surface.

The unsaturated zone communication device 190 is connected to the unsaturated zone $CO_2$ concentration measuring sensor 185 to transmit information of the $CO_2$ concentration output from the unsaturated zone $CO_2$ concentration measuring sensor 185 to the monitoring server 195 through a wired communication scheme or a wireless communication scheme.

Meanwhile, the monitoring server 195 stores reference $CO_2$ concentration provided at the unsaturated zone and the near-surface atmosphere according to time slots. In addition, the monitoring server 195 compares the measured $CO_2$ concentration C_detect, which is transmitted from the communication devices 17 and 190 for the near-surface atmosphere and the unsaturated zone, with the reference $CO_2$ concentration C_ref of each time slot which has been previously stored and outputs a normal signal or an abnormal signal through a monitor or a printer. In addition, the monitoring server 195 can directly output the measured $CO_2$ concentration and store the information of the measured $CO_2$ concentration in a storage space.

The monitoring server 195 compares the measured $CO_2$ concentration C_detect, which is transmitted, with the reference $CO_2$ concentration C_ref corresponding to a time slot in which the $CO_2$ concentration is measured. The monitoring server 195 may generate an abnormal signal if the measured $CO_2$ concentration C_detect is greater than the reference $CO_2$ concentration C_ref.

In this case, the monitoring server 195 may generate the abnormal signal when the measured $CO_2$ concentration C_detect is greater than or equal to a value obtained by adding a specific numeric value a to the reference $CO_2$ concentration C_ref (C_detect≥C_ref+α).

In addition, the monitoring server 195 may generate the abnormal signal when the measured $CO_2$ concentration C_detect is greater than or equal to a value obtained by multiplying a specific ratio β% (β is a value greater than 1) to the reference $CO_2$ concentration C_ref (C_detect≥β×C_ref).

In order to perform the above operation, as shown in FIG. 2, the monitoring server 195 may include an input module 210, a data storing module 220, a comparison module 230, and an output module 240.

The input module 210 receives the information of the measured $CO_2$ concentration C_detect from the near-surface atmosphere communication device 170 and the unsaturated zone communication device 190. The data storing module 220 stores the reference $CO_2$ concentration C_ref for each time slot.

The comparison module 230 receives the measured $CO_2$ concentration C_detect from the input module 210 and receives the reference $CO_2$ concentration C_ref from the data storing module 220 to compare the measured $CO_2$ concentration C_detect with the reference $CO_2$ concentration C_ref, thereby outputting a result signal expressed as "0" and "1" or "LOW" and "HIGH".

The output module 240 may output the normal signal or the abnormal signal to an output device such as a monitor or a printer according to the result signal.

Meanwhile, the monitoring server 195 may be connected to an alarm device (not shown). The alarm device sounds a warning such as a siren or an alarm in response to the abnormal signal of the monitoring server 195 so that a manager or a worker can recognize the leakage of $CO_2$.

Although FIG. 1 shows only the system 100 for monitoring unsaturated zone gas, and the concentration of $CO_2$ and isotopes at the near-surface atmosphere for the purpose of explanation, the present invention is naturally applicable to the monitoring of the $CO_2$ concentration and the isotopes at the near-surface atmosphere without the unsaturated zone $CO_2$ concentration detector 180 and the unsaturated zone communication device 190.

Figure 3:
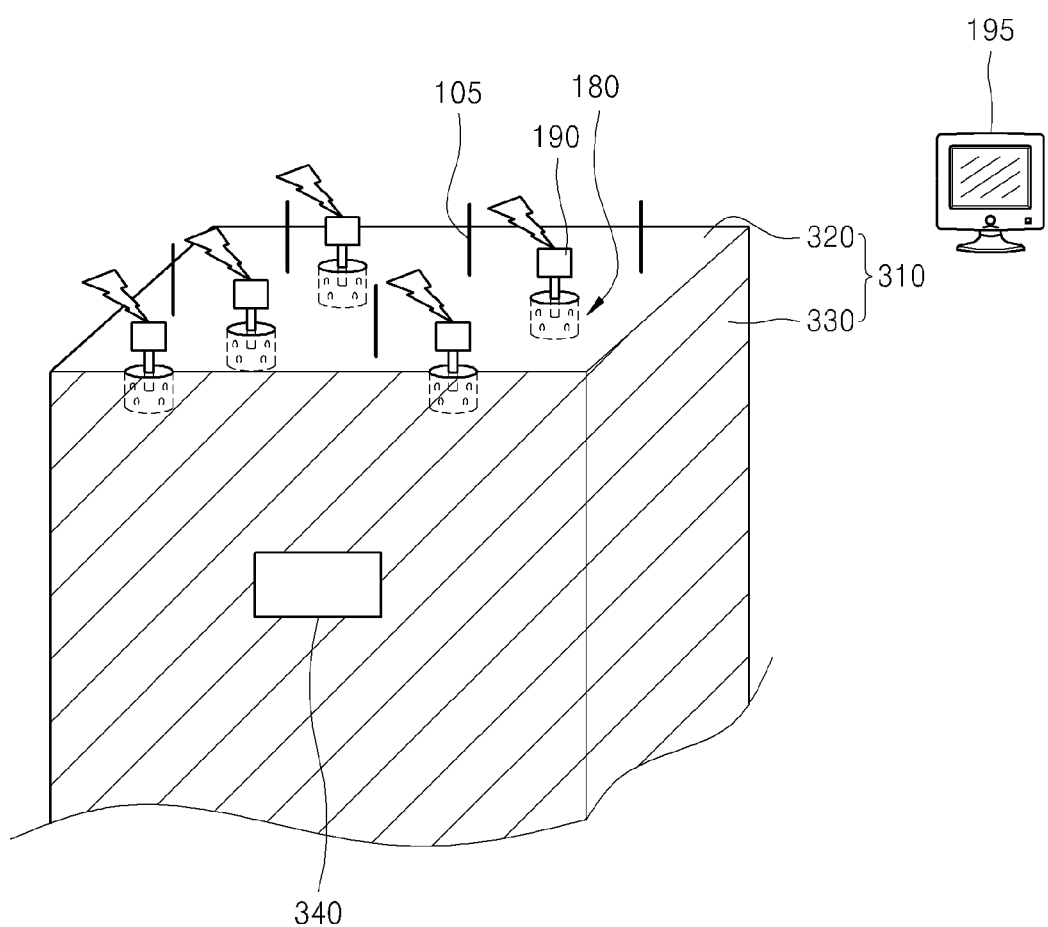
FIG. 3 is a view schematically showing a system for monitoring the concentration of carbon dioxide and isotopes at the land under which the carbon dioxide is stored according to the present invention.

FIG. 3 is a view schematically showing a system for monitoring the $CO_2$ concentration and isotopes at the land under which the $CO_2$ is stored according to the present invention.

Referring to FIG. 3, the system shown in FIG. 3 for monitoring the $CO_2$ concentration and isotopes at the land under which the $CO_2$ is stored includes a plurality of near-surface atmosphere analyzers 105 installed on a ground surface 320 of a $CO_2$ storing land 310 under which $CO_2$ is stored, a plurality of unsaturated zone $CO_2$ concentration detectors 180 buried in the unsaturated zone of an underground soil layer 330 at the $CO_2$ storing land 310, a plurality of near-surface atmosphere communication devices (not shown) connected to the near-surface atmosphere analyzers 105, a plurality of unsaturated zone communication devices 190 connected to the unsaturated zone $CO_2$ concentration detectors 180, and the monitoring server 195.

The $CO_2$ storing land 310 is provided therein with an underground $CO_2$ reservoir 340 which is located at a deep part of the underground soil layer 330, that is, at a region of about 800 m of the underground soil layer 330 to capture and store CO2 which has been discharged from manufacturers.

In this case, the near-surface atmosphere analyzers 105 are arranged on the ground surface 320 of the $CO_2$ storing land 310 perpendicularly to the underground $CO_2$ reservoir 340. The unsaturated zone $CO_2$ concentration detectors 180 are arranged in an unsaturated zone provided on the underground soil layer 330 perpendicularly to the underground $CO_2$ reservoir 340. In addition, since the $CO_2$ may be discharged to the peripheral portion of the $CO_2$ storing land 310, the near-surface atmosphere analyzers 105 and the unsaturated zone $CO_2$ concentration detectors 180 are preferably provided at a surrounding land as well as the $CO_2$ storing land 310.

Meanwhile, $CO_2$ transient storage facilities, pressurizing facilities, temperature boosting facilities, and injection facilities may be provided on the $CO_2$ storing land 310.

Since the near-surface atmosphere analyzer 105, the unsaturated zone $CO_2$ concentration detector 180, the near-surface atmosphere communication device 170, the unsaturated zone communication device 190, and the monitoring server 195 have the structures the same as those of FIG. 1, the details thereof will be omitted.

When the near-surface atmosphere analyzers 105 and the unsaturated zone $CO_2$ concentration detectors 180 are applicable to the $CO_2$ storing land 310, the isotopes at the unsaturated zone and the near-surface atmosphere can be monitored in real time together with the unsaturated zone gas and the $CO_2$ concentration of the near-surface atmosphere, so that the behavior of the $CO_2$ can be observed with reliability. Therefore, when $CO_2$ stored under the ground leaks, the action according to the leakage of $CO_2$ can be instantly performed.

As described above, the system for monitoring the $CO_2$ concentration and isotopes at the land under which the $CO_2$ is stored, which has mainly monitored only an injection stratum of the $CO_2$ storing land 310, can monitor the unsaturated zone and the near-surface atmosphere of the $CO_2$ storing land 310. In addition, as the leakage state of $CO_2$, which has been stored under the ground, can be economically monitored in real time with reliability by using an isotope analyzer and the $CO_2$ concentration measuring sensor, the action according to the leakage of $CO_2$ can be rapidly performed, and the stability of ground equipment can be ensured.

Figure 4:
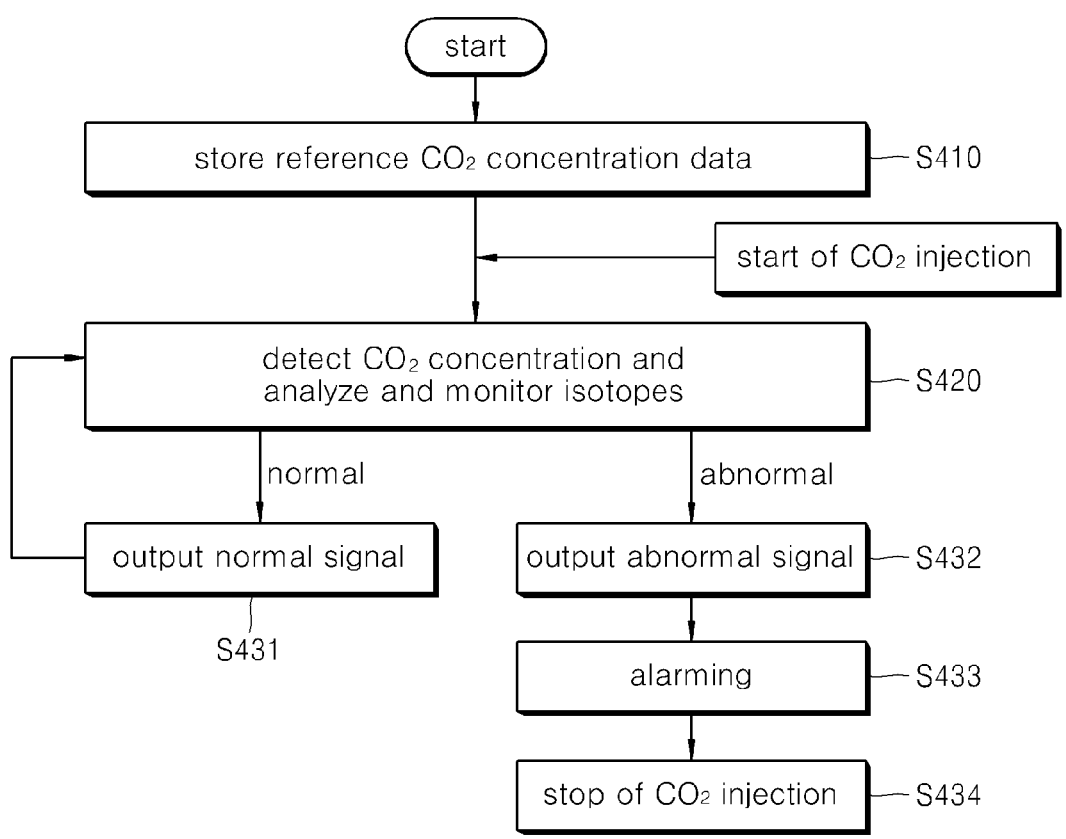
FIG. 4 is a flowchart showing a method of monitoring the unsaturated zone gas and the concentration of the carbon dioxide and the isotopes at the near-surface atmosphere according to one embodiment of the present invention.

FIG. 4 is a flowchart showing a method of monitoring the unsaturated zone gas and the concentration of the $CO_2$ and the isotopes at the near-surface atmosphere according to one embodiment of the present invention.

Referring to FIG. 4, the method of monitoring the unsaturated zone gas and the concentration of the $CO_2$ and the isotopes at the near-surface atmosphere includes a step of storing reference $CO_2$ concentration data (S410), a step of detecting $CO_2$ concentration, and analyzing and monitoring isotopes (S420), and a step of outputting a result signal (S431 and S432).

According to the step of storing the reference $CO_2$ concentration data (S410), before $CO_2$ is stored under the ground, the concentration of $CO_2$ existing at the unsaturated zone and the concentration of $CO_2$ existing at the near-surface atmosphere are measured according to time slots, transferred to the monitoring server through the communication device, and analyzing the information of the unsaturated zone gas and the concentration of $CO_2$ existing at the near-surface atmosphere, thereby storing the maximum concentration of $CO_2$, which can be obtained from the nature, as the reference $CO_2$ concentration.

The concentration of $CO_2$ existing at the unsaturated zone is measured by using the unsaturated zone $CO_2$ concentration detector 180 buried in the unsaturated zone under the ground surface as shown in FIG. 1. The concentration of $CO_2$ existing at the near-surface atmosphere is measured by using the near-surface atmosphere $CO_2$ concentration measuring sensor 151 of the near-surface atmosphere analyzer 105 erected on the ground surface as shown in FIG. 1.

The reasons that the reference $CO_2$ concentration is previously stored are as follows. The concentration of the $CO_2$ existing at the unsaturated zone is frequently varied according to the biological activity made in the soil, a physical-chemical phenomenon exerting an influence on the biological activity, a season, day and night, and other physical-chemical conditions. In addition, the concentration of the $CO_2$ existing at the near-surface atmosphere is frequently varied according to day and night and other physical-chemical conditions. Therefore, the generalization of the concentration of the CO2 existing at the unsaturated zone and the near-surface atmosphere is very difficult. Therefore, reference concentration of $CO_2$ obtained from the nature is previously detected by measuring the concentration of $CO_2$ existing at a specific position in the unit of time for at least one year in order to determine the leakage state of the injected $CO_2$ and then the action for the leakage of the $CO_2$ is required when an abnormal value beyond the reference concentration is measured.

According to the step of detecting $CO_2$ concentration, and analyzing and monitoring isotopes (S420), after starting the storage of $CO_2$ under the ground, the concentration of the $CO_2$ contained in the unsaturated zone gas is measured by the unsaturated zone $CO_2$ concentration detector 180 shown in FIG. 1, and the concentration of the $CO_2$ existing at the near-surface atmosphere is measured by the near-surface atmosphere analyzer 105 erected on the ground surface. Then, the concentration of the $CO_2$ existing at the unsaturated zone gas and the near-surface atmosphere is transmitted to the monitoring server 195 through the near-surface atmosphere communication device 170 and the unsaturated zone communication device 190. The concentration of the $CO_2$ measured at each of the unsaturated zone gas and the near-surface atmosphere is compared with the reference $CO_2$ concentration at each of the unsaturated zone gas and the near-surface atmosphere.

In addition, the isotope analyzer 153 of the near-surface atmosphere analyzer 105 shown in FIG. 1 analyzes the isotopes existing near-surface atmosphere gas including at least one of $CO_2$, $CH_4$, $H_2O$, $SO_X$, and $H_2S$ and transmits the information of the isotopes to the monitoring server 195 through the communication device 170 shown in FIG. 1.

In addition, the unsaturated zone $CO_2$ concentration measuring sensor 185, for example, the NDIR sensor is connected to the analyzing member 150 of the near-surface atmosphere analyzer 105 to measure the isotopes of the unsaturated zone or the isotopes of the unsaturated zone gas by using the isotope analyzer 153, and to transmit the information of the isotopes to the monitoring server 195 through the communication device 170 of FIG. 1.

According to the step of outputting the result signal (S431 and S432), the monitoring server 195 outputs a normal signal or an abnormal signal by using the comparison result of the measured $CO_2$ concentration and the reference $CO_2$ concentration. The monitoring server compares the measured $CO_2$ concentration with the reference $CO_2$ concentration. Accordingly, the monitoring server may generate the abnormal signal if the measured $CO_2$ concentration is greater than or equal to the sum of a predetermined value of the reference $CO_2$ concentration or a value obtained by multiplying a specific numeric value or a specific ratio to the reference $CO_2$ concentration.

If the abnormal signal is output from the monitoring server, a step S433 of outputting an alarm is additionally provided, so that the injection of $CO_2$ can be stopped (step S434).

As described above, according to the method of monitoring the unsaturated zone gas and the concentration of the $CO_2$ and the isotopes at the near-surface atmosphere, in the state that the reference $CO_2$ concentration is measured at the unsaturated zone and the near-surface atmosphere according to the time slots and stored before $CO_2$ is stored under the ground, the reference $CO_2$ concentration is compared with the $CO_2$ concentration which is detected at the unsaturated zone and the near-surface atmosphere in real time, thereby easily distinguishing the variation of the $CO_2$ concentration according to the variation of environments from the variation of the $CO_2$ concentration caused by the leakage of the $CO_2$ stored under the ground.

In addition, as well as the measurement of $CO_2$ concentration, isotopes of gas contained in the unsaturated zone gas and the near-surface atmosphere are analyzed in real time by using an isotope analyzer, thereby economically monitoring the leakage state of $CO_2$ stored under the ground with reliability in real time, so that the action according to the leakage of $CO_2$ can be rapidly performed, and the stability of ground equipment can be ensured.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A system for monitoring an unsaturated zone gas and a near-surface atmosphere, the system comprising:
   a near-surface atmosphere analyzer including a fixing member erected on a ground surface, a plurality of near-surface gas inlets fixed to the fixing member according to heights of the near-surface gas inlets, a plurality of gas transfer members communicating with the near-surface gas inlets, an analyzing member including an isotope analyzer, which analyzes an isotope of gas transferred through the gas transfer members, a channel connected to the gas transfer members and the analyzing member to select one gas transfer member and to supply gas transferred through the selected gas transfer member to the analyzing member, and a connection member connecting the channel to the analyzing member;
   a communication device transmitting components of the isotope output from the isotope analyzer; and
   a monitoring server outputting the components of the isotope transmitted from the communication device.

2. The system of claim 1, wherein the gas includes at least one of carbon dioxide ($CO_2$), methanol ($CH_4$), vapor ($H_2O$), sulfiding gas ($SO_x$), and hydrogen sulfide ($H_2S$).

3. The system of claim 1, wherein the isotope analyzer employs one of a wavelength-scanned cavity ring down spectroscopy (WS-CRDS) scheme and an integrated cavity output spectroscopy (ICOS) scheme that allow the isotopes to be analyzed in real time.

4. The system of claim 3, further comprising an unsaturated zone $CO_2$ concentration detector buried in an unsaturated zone under the ground surface and including a chamber having a shape of a tub, a gas inlet formed at a lateral side of the chamber, and an unsaturated $CO_2$ concentration measuring sensor provided through an upper portion of the chamber to measure concentration of $CO_2$ contained in gas of the chamber.

5. The system of claim 4, wherein the monitoring server compares the measured concentration of the $CO_2$, which is transmitted from each of the near-surface atmosphere $CO_2$ concentration measuring sensor and the unsaturated zone $CO_2$ concentration measuring sensor, with reference $CO_2$ concentration and generates an abnormal signal if the measured concentration of the $CO_2$ is greater than the reference $CO_2$ concentration by a predetermined value or greater than a specific numeric value or a specific ratio.

6. The system of claim 5, wherein the monitoring server includes an alarm device to output an alarm in response to the abnormal signal.

7. The system of claim 5, wherein the near-surface atmosphere $CO_2$ concentration measuring sensor and the unsaturated zone $CO_2$ concentration measuring sensor include a non dispersive infra-red (NDIR) sensor.

8. The system of claim 7, wherein the unsaturated zone $CO_2$ concentration measuring sensor is connected to the analyzing member.

9. The system of claim 1, wherein the analyzing member further includes a near-surface atmosphere $CO_2$ concentration measuring sensor to measure concentration of $CO_2$ contained in a near-surface atmosphere gas supplied through the channel.

10. The system of claim 9, wherein the near-surface atmosphere $CO_2$ concentration measuring sensor and the unsaturated zone $CO_2$ concentration measuring sensor include a non dispersive infra-red (NDIR) sensor.

11. The system of claim 10, wherein the unsaturated zone $CO_2$ concentration measuring sensor is connected to the analyzing member.

12. The system of claim 1, wherein the system is applied to a land under which $CO_2$ is stored.

13. A method of monitoring an unsaturated zone gas and a near-surface atmosphere at a land under which $CO_2$ is stored, the method comprising:
   (a) measuring concentration of $CO_2$ at an unsaturated zone in a land to be used to store $CO_2$ under a ground according to time slots in a $CO_2$ concentration detector, transmitting the concentration of $CO_2$ to a monitoring server through a communication device, analyzing information of the concentration of $CO_2$ at the unsaturated zone in the monitoring server, and storing a maximum of the concentration of $CO_2$, which is obtained from a nature, as a reference concentration of $CO_2$ at the unsaturated zone, before CO2 is stored under the ground;
   (b) analyzing isotopes of gas contained in a near-surface atmosphere in an isotope analyzer of a near-surface atmosphere analyzer, measuring the concentration of $CO_2$ at the unsaturated zone in the $CO_2$ concentration detector, and transmitting the concentration of $CO_2$ to the monitoring server through the communication device, after the storage of the $CO_2$ under the ground is started; and
   (c) comparing the measured concentration of the CO2 with the reference concentration of $CO_2$ in the monitoring server and outputting a normal signal or an abnormal signal.

14. The method of claim 13, wherein step (a) includes measuring concentration of $CO_2$ at a near-surface atmosphere in the land to be used to store $CO_2$ under the ground according to time slots in a near-surface atmosphere $CO_2$ concentration measuring sensor of a near-surface atmosphere analyzer, transmitting the concentration of $CO_2$ to the monitoring server through the communication device, analyzing information of the concentration of $CO_2$ at the near-surface atmosphere in the monitoring server, and storing a maximum of the concentration of $CO_2$, which is obtained from the nature, as a reference concentration of $CO_2$ at the near-surface atmosphere.

15. The method of claim 14, wherein step (b) includes measuring the concentration of CO2 at the near-surface atmosphere in the near-surface atmosphere $CO_2$ concentration measuring sensor and transmitting the concentration of $CO_2$ at the near-surface atmosphere to the monitoring server through the communication device.

16. The method of claim 13, wherein step (b) includes connecting the unsaturated zone $CO_2$ concentration measuring sensor of a $CO_2$ concentration detector to an analyzing member of the near-surface atmosphere analyzer, measuring isotopes at the unsaturated zone or isotopes of unsaturated zone gas by using the isotope analyzer, and transmitting information of the isotopes to the monitoring server through the communication device.

* * * * *